(12) United States Patent
Tamamori et al.

(10) Patent No.: US 9,377,618 B2
(45) Date of Patent: Jun. 28, 2016

(54) ELECTROSTATIC COMB ACTUATOR, DEFORMABLE MIRROR USING THE ELECTROSTATIC COMB ACTUATOR, ADAPTIVE OPTICS SYSTEM USING THE DEFORMABLE MIRROR, AND SCANNING LASER OPHTHALMOSCOPE USING THE ADAPTIVE OPTICS SYSTEM

(71) Applicant: CANON KABUSHIKI KAISHA, Tokyo (JP)

(72) Inventors: Kenji Tamamori, Ebina (JP); Hiroyuki Ozaki, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/569,904

(22) Filed: Dec. 15, 2014

(65) Prior Publication Data

US 2015/0098062 A1 Apr. 9, 2015

Related U.S. Application Data

(62) Division of application No. 14/060,888, filed on Oct. 23, 2013, now Pat. No. 8,944,598.

(30) Foreign Application Priority Data

Nov. 13, 2012 (JP) .................................. 2012-248936

(51) Int. Cl.
*A61B 3/14* (2006.01)
*A61B 3/10* (2006.01)
*G02B 26/08* (2006.01)
(Continued)

(52) U.S. Cl.
CPC .......... *G02B 26/0841* (2013.01); *A61B 3/1025* (2013.01); *A61B 3/12* (2013.01); *A61B 3/1225* (2013.01); *G02B 26/0825* (2013.01); *H02N 1/002* (2013.01); *H02N 1/008* (2013.01)

(58) Field of Classification Search
USPC .................................................. 351/200–246
See application file for complete search history.

(56) References Cited

U.S. PATENT DOCUMENTS 6,609,794 B2  8/2003  Levine
7,476,561 B2  1/2009  Mori et al.
7,476,948 B2  1/2009  Mori et al.
(Continued)

FOREIGN PATENT DOCUMENTS

JP  2005-279919 A  10/2005
JP  2010-008613 A  1/2010
JP  2010-107628 A  5/2010

*Primary Examiner* — Mohammed Hasan
(74) *Attorney, Agent, or Firm* — Fitzpatrick, Cella, Harper & Scinto

(57) ABSTRACT

Provided is an actuator formed in a substrate including a handle layer, an elastic body layer, and an insulating layer, the actuator including a movable portion supported to a support portion by an elastic body, a movable comb electrode formed on the movable portion, a fixed comb electrode supported by the support portion, and electrode wirings connected to the respective comb electrodes in which the elastic body supports the movable portion such that the movable portion is displaceable in a direction perpendicular to the substrate in accordance with voltages applied to the comb electrodes; the comb electrodes are made up of the handle layer, and the elastic body is made up of the elastic body layer; and a handle layer separation groove is provided to electrically separate between the handle layers of the support portions supporting the comb electrodes, and a structure reinforcing portion is formed across the separation groove.

20 Claims, 3 Drawing Sheets

(51) Int. Cl.
*A61B 3/12* (2006.01)
*H02N 1/00* (2006.01)

(56) References Cited

U.S. PATENT DOCUMENTS

| | | |
|---|---|---|
| 8,279,509 B2 | 10/2012 | Maruyama et al. |
| 2005/0194840 A1 | 9/2005 | Mori et al. |
| 2006/0186498 A1 | 8/2006 | Mori et al. |
| 2010/0103492 A1 | 4/2010 | Maruyama et al. |
| 2012/0218613 A1 | 8/2012 | Maruyama et al. |
| 2013/0265546 A1* | 10/2013 | Nozato ............ A61B 3/14 351/206 |
| 2014/0125950 A1* | 5/2014 | Shimada ......... G02B 26/0841 351/206 |
| 2014/0232984 A1* | 8/2014 | Tamamori ......... A61B 3/14 351/206 |

* cited by examiner

ELECTROSTATIC COMB ACTUATOR, DEFORMABLE MIRROR USING THE ELECTROSTATIC COMB ACTUATOR, ADAPTIVE OPTICS SYSTEM USING THE DEFORMABLE MIRROR, AND SCANNING LASER OPHTHALMOSCOPE USING THE ADAPTIVE OPTICS SYSTEM

This application is a division of application Ser. No. 14/060,888 filed Oct. 23, 2013.

BACKGROUND OF THE INVENTION

1. Field of the Invention

The present invention relates to an electrostatic comb actuator in a MEMS field or the like, and more particularly, to an electrostatic comb actuator that is applicable to, for example, a deformable mirror. Moreover, the present invention relates to an adaptive optics system using the deformable mirror, and a scanning laser ophthalmoscope using the adaptive optics system.

2. Description of the Related Art

An electrostatic comb actuator is one of drive units having a fine mechanical structure, and can perform micro-driving in accordance with a potential difference between comb electrodes. Further, the electrostatic comb actuator is also applicable to sensing by measuring the change in distance between comb teeth, which is caused by external factors, as a change in electrostatic capacitance. The electrostatic comb actuator can thus be used as a micro-driving unit and a sensor structure, and hence is expected to be applied as a structure capable of realizing downsizing and integration of an element in technical fields such as information and communication, medical care and biotechnology, automobiles, and robots.

A general electrostatic comb actuator is next described. Japanese Patent Application Laid-Open No. 2010-008613 proposes an electrostatic comb actuator structure in which a movable comb electrode, a fixed comb electrode, and an elastic body are formed in a device layer of a semiconductor substrate, and a separation groove for the electrodes is formed in a handle layer of the semiconductor substrate.

Japanese Patent Application Laid-Open No. 2010-008613 discloses that a movable comb electrode, a fixed comb electrode, and a beam (hinge) are made up of a device layer of an SOI substrate (semiconductor substrate), which has a thickness of, for example, about 30 μm. The electrostatic comb actuator is configured to rotate a movable portion about an axis formed by the beam. Considering application of the above-mentioned configuration to a configuration for displacing the movable portion in a direction perpendicular to the substrate, in order to increase the displacement amount of the movable portion, the beam needs to be thinned. However, in this case, when the beam is thinned, the comb electrodes are also thinned. As a result, sufficient displacement amount may not be obtained. Further, in the configuration disclosed in Japanese Patent Application Laid-Open No. 2010-008613, a handle layer separation groove is formed as the electrode separation groove, and a connection portion in the separation groove is made up of a silicon device layer which has a thickness of, for example, about 30 μm. However, considering the above-mentioned configuration, thinning the beam results in reduction in strength of the connection portion.

SUMMARY OF THE INVENTION

The present invention has been made in order to solve the above-mentioned problem, and has an object to provide, for example, an electrostatic comb actuator capable of increasing a displacement amount of a movable portion in a direction perpendicular to a substrate, and increasing the strength of a connection portion in a separation groove for electrodes.

According to one embodiment of the present invention, there is provided an electrostatic comb actuator, which is formed in a substrate including a handle layer, an elastic body layer, and an insulating layer sandwiched between the handle layer and the elastic body layer. The electrostatic comb actuator includes: a support portion; a movable portion supported to the support portion by an elastic body; a movable comb electrode formed on the movable portion; a fixed comb electrode supported by the support portion; and electrode wirings connected separately to the movable comb electrode and the fixed comb electrode. Then, the elastic body supports the movable portion in such a manner that the movable portion is displaceable in a direction perpendicular to the surface (in a direction perpendicular to a surface of the substrate) in accordance with voltages applied to the movable comb electrode and the fixed comb electrode. The movable comb electrode, the fixed comb electrode, and the support portion are each made up of the handle layer, and the elastic body is made up of the elastic body layer. Further, the handle layer is provided with a handle layer separation groove for electrically separating the handle layer of the movable comb electrode from the handle layer of the support portion supporting the fixed comb electrode. The actuator further comprises a structure reinforcing portion and provided across the handle layer separation groove.

Further features of the present invention will become apparent from the following description of exemplary embodiments with reference to the attached drawings.

DESCRIPTION OF THE EMBODIMENTS

The present invention has the following features. Movable and fixed comb electrodes are made up of a handle layer of a substrate. An elastic body for supporting a movable portion with respect to a support portion is made up of an elastic body layer of the substrate. A structure reinforcing portion is formed across a handle layer separation groove for separating between the handle layers of the support portions for supporting the movable and fixed comb electrodes. With this, the movable comb electrode and the fixed comb electrode can be made up of the thick handle layer of the substrate, and the elastic body can be made up of the thin elastic body layer of the substrate. Thus, the displacement amount of the movable portion in a direction perpendicular to the substrate can be increased. Further, at the connection portion in the handle layer separation groove, the structure reinforcing portion is formed as described above, and thus the strength of the connection portion can be increased.

The structure reinforcing portion is an insulating material portion that is filled in the separation groove, or an insulating material layer formed in contact with the elastic body layer on the opposite side to the handle layer in a region including a part corresponding to the separation groove. However, any structure reinforcing portion may be formed as long as the structure reinforcing portion can reinforce reduction in strength of the handle layer due to the separation groove while maintaining the electric separation. If permitted in design considering the application of the electrostatic comb actuator, for example, the structure reinforcing portion may be an insulating material layer formed across the separation groove and in contact with the handle layer in the region including the part corresponding to the separation groove.

Configurations and actions and effects of the present invention are described by way of embodiments of the present invention.

Figure 1:
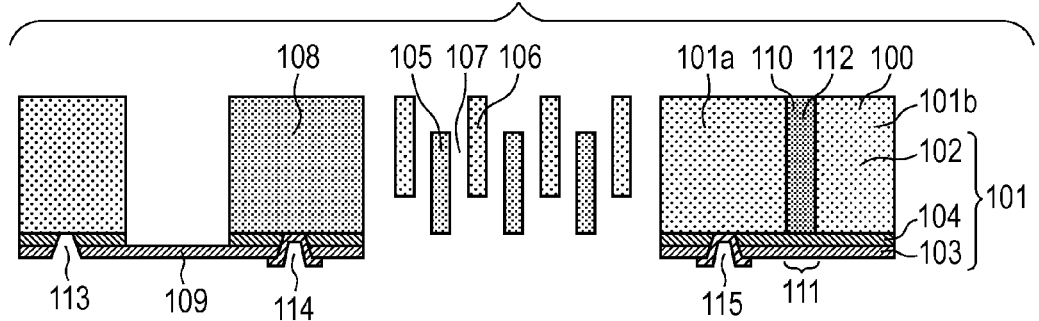
FIG. 1 is a sectional view illustrating an electrostatic comb actuator according to Example 1 of the present invention.
Figure 2A:
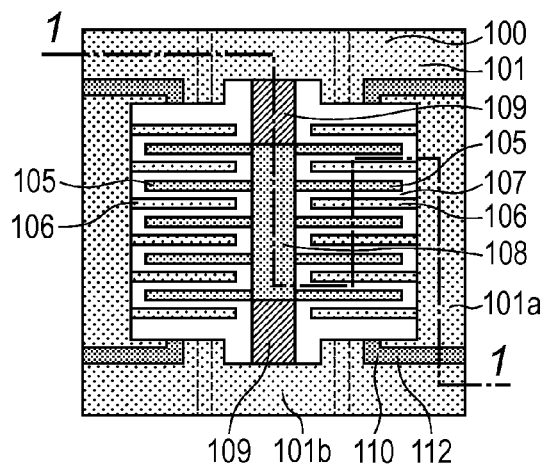
FIGS. 2A and 2B are plan views illustrating the electrostatic comb actuator according to Example 1 of the present invention.
Figure 2B:
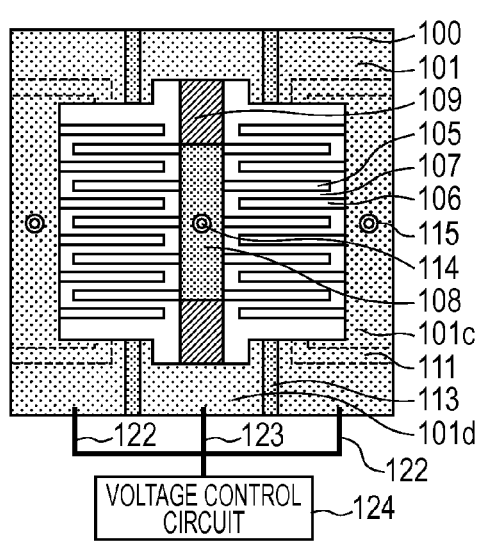

In the following, with reference to FIGS. 1, 2A, 2B, and 3A to 3D, the point of view of the present invention is described in detail. FIG. 1 is a sectional view of an electrostatic comb actuator according to the present invention. FIGS. 2A and 2B are plan views of the electrostatic comb actuator according to the present invention. FIG. 2A illustrates a front surface, and FIG. 2B illustrates a rear surface. Further, FIG. 1 corresponds to a cross section taken along the line 1-1 of FIG. 2A.

An electrostatic comb actuator 100 is formed in a substrate 101. The substrate 101 includes a handle layer 102, an elastic body layer 103, and an insulating layer 104 formed between the handle layer and the elastic body layer. The handle layer 102 of the substrate 101 is made of, for example, p-type monocrystalline silicon having a crystal plane orientation of (100), and has a thickness of, for example, 200 μm and a resistivity of, for example, 0.01 Ωcm to 0.02 Ωcm. The elastic body layer 103 of the substrate 101 is made of, for example, p-type monocrystalline silicon having a crystal plane orientation of (100), and has a thickness of 1 μm and a resistivity of 0.01 Ωcm to 0.02 Ωcm. The insulating layer 104 of the substrate 101 is made of, for example, silicon oxide, and has a thickness of, for example, 2 μm. The type, crystal plane orientation, thickness, resistivity of the silicon and the material and thickness of the insulating layer described above are merely examples, and the present invention is not limited thereto.

As illustrated in FIGS. 2A and 2B, in the electrostatic comb actuator 100, a movable comb electrode 105 and a fixed comb electrode 106 are arranged so as to be opposed to each other and separated from each other by a comb electrode separation groove 107, and comb teeth thereof are arranged so as to be alternately arrayed. Further, each of the comb electrodes is arranged in line symmetry with respect to a movable portion 108. The movable comb electrode 105, the fixed comb electrode 106, and the comb electrode separation groove 107 are formed in the thick handle layer 102 so that a large electric capacitance can be taken between those comb electrodes. Those comb shapes are formed perpendicular to the horizontal direction of the substrate 101 (perpendicular to the surface of the substrate). The movable comb electrode 105 is supported by the handle layer 102 of the movable portion 108, and the fixed comb electrode 106 is supported by the handle layer 102 of a region 101a of the substrate 101. The movable comb electrode 105, the fixed comb electrode 106, and the comb electrode separation groove 107 each have a width of, for example, 5 μm. The movable comb electrode 105 and the fixed comb electrode 106 each have a length in a direction horizontal to the substrate of, for example, 200 μm. Those values are merely examples, and the present invention is not limited to those values.

Next, as illustrated in FIG. 2B, an elastic body layer separation groove 113 electrically insulates an elastic body layer 101d having the same potential as the movable comb electrode 105 from an elastic body layer 101c having the same potential as the fixed comb electrode 106. An insulating material may be filled in the elastic body layer separation groove 113. A contact hole 114 electrically connects between the handle layer 102 of the movable portion 108 supporting the movable comb electrode 105 and the elastic body layer 103 of the movable portion 108. Further, a contact hole 115 electrically connects the handle layer 101a supporting the fixed comb electrode 106 and the elastic body layer 101c. The movable comb electrode 105 and the fixed comb electrode 106 are electrically insulated from each other, and are connected to a voltage control circuit 124 via fixed comb electrode wiring 122 and movable comb electrode wiring 123, respectively, which are separately connected to respective support portions in order to apply potentials through the respective support portions.

Next, as illustrated in FIG. 2A, an elastic body 109 supports the movable portion 108 in such a manner that the movable portion 108 is displaceable in a direction perpendicular to the horizontal surface of the substrate 101 (direction perpendicular to the surface of the substrate), and supports the movable portion 108 from two horizontal directions of the substrate 101 in line symmetry with respect to the movable portion 108. The movable portion 108 is prevented from being displaced in an unnecessary direction other than the direction perpendicular to the substrate by the symmetric property of the movable comb electrode 105 and the fixed comb electrode 106 and the symmetric property of the elastic body 109 with respect to the movable portion 108.

Next, in order to upwardly drive the movable portion 108 in the direction perpendicular to the substrate, as illustrated in FIG. 1, arrangement is made so that the movable comb electrode 105 is located on the lower side with respect to the fixed comb electrode 106 in the perpendicular direction. The movable comb electrode 105 and the fixed comb electrode 106 are formed to have level differences in the direction perpendicular to the substrate at positions of respective upper surfaces and lower surfaces. That is, on the front surface side of the substrate 101, arrangement is made so that the upper position of the fixed comb electrode 106 is located on the upper side with respect to the upper position of the movable comb electrode 105 in the perpendicular direction, and this level difference is, for example, 10 μm. On the other hand, on the rear surface side of the substrate 101, arrangement is made so that the lower position of the fixed comb electrode 106 is located on the upper side with respect to the lower position of the movable comb electrode 105 in the perpendicular direction, and this level difference is, for example, 10 μm, which is the same as that on the front surface side. The reason is because this embodiment employs a type in which, when the comb electrodes are attracted to each other by an electrostatic attractive force, a force acts and displacement occurs in a direction in which the above-mentioned level difference between the comb teeth is eliminated. Note that, this type has such a structure that, when the comb electrodes are entirely overlapped with each other, the movable portion that integrally moves with the movable comb electrode is not displaced any more, and hence an overlapping part when a voltage is applied increases as compared to an overlapping part in an initial position. Further, the movable comb electrode 105 and the fixed comb electrode 106 have the same thickness (in the direction perpendicular to the substrate), and for example, the thickness thereof is 190 μm in this case. The above-mentioned level difference and comb electrode thickness are merely examples, and the present invention is not limited to those values.

Next, the elastic body 109 is formed in the thin elastic body layer 103 of the substrate 101 in order to increase the displacement of the movable portion 108. In this case, the shape of the elastic body 109 is, for example, a plate spring structure, and the width and the length thereof are, for example, 40 μm and 200 μm, respectively. The elastic body 109 is made up of the elastic body layer 103 made of, for example, monocrystalline silicon, and hence the elastic body 109 has good mechanical characteristics as a spring. The thickness of the elastic body 109 is 1 μm. The shape and dimension of the elastic body 109 are merely examples, and the present invention is not limited thereto.

Next, a handle layer separation groove 110 electrically separates between a handle layer 101b of the substrate 101, which is connected to the elastic body 109 supporting the movable comb electrode 105, and the handle layer 101a of the substrate 101, which is connected to the fixed comb electrode 106. The handle layer 101a and the handle layer 101b are connected to each other with a connection portion 111 made up of the same elastic body layer 103 as the elastic body 109 (which is located immediately below the separation groove 110) through intermediation of the insulating layer 104 formed immediately below the handle layer 101a and the handle layer 101b. The thickness of the connection portion 111 is the same as that of the elastic body 109. When the elastic body layer 103 is thinned to increase the displacement of the movable portion 108 in the perpendicular direction, the strength of the connection portion 111 is reduced as the connection portion 111 becomes thinner. Therefore, a structure reinforcing portion 112 is provided across the handle layer separation groove 110 separately from the elastic body layer 103 in order to increase the strength of the connection portion 111 even when the elastic body layer 103 is thin. For example, as illustrated in FIG. 1, the insulating layer 104 between the handle layer and the elastic body layer is left unremoved, and the handle layer separation groove 110 is filled with an insulating material. Alternatively, there is provided a member that is formed across the handle layer separation groove 110 and in contact with the elastic body layer on the opposite side to the handle layer 102. With this structure reinforcing portion 112, the thickness of the connection part provided across the separation groove 110 increases, and hence even when the elastic body layer 103 is thin, the strength of the connection portion 111 can be increased while achieving electrode separation.

In this case, as a material filled in the handle layer separation groove 110, for example, silicon oxide is used, and silicon oxide whose raw material is tetraethoxysilane (TEOS)/ozone ($O_3$) and formed by a plasma chemical vapor deposition (CVD) may be used. In addition, phosphorus silicate glass (PSG), boron silicate glass (BSG), boron phosphorus silicate glass (BPSG), and spin on glass (SOG) may be used. Further, the material filled in the handle layer separation groove 110 may have a multilayered structure obtained by forming a polysilicon film after a silicon thermally-oxidized film is formed on a side wall of the handle layer separation groove 110, or may contain silicon nitride. Alternatively, an insulating resin may be used, such as resins including an epoxy-based resin and benzocyclobutene (BCB). Those materials are merely examples, and the present invention is not limited to those materials.

Figures 3A, 3B, 3C, 3D:
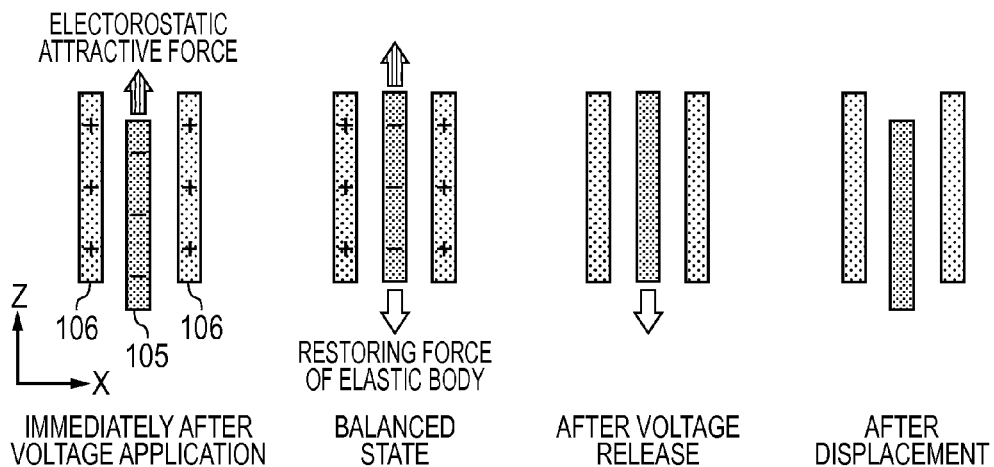
FIGS. 3A, 3B, 3C, and 3D are sectional views illustrating a method of driving the electrostatic comb actuator according to the present invention.

Next, FIGS. 3A to 3D are sectional views illustrating a method of driving the electrostatic comb actuator according to the present invention, and simply illustrate merely the movable comb electrode 105 and the fixed comb electrode 106 as the structure of the electrostatic comb actuator. As illustrated in FIG. 3A, immediately after voltage application, due to an electrostatic attractive force generated between the comb electrodes by applying charges of opposite signs to the movable comb electrode 105 and the fixed comb electrode 106, respectively, the movable comb electrode 105 is displaced upwardly in the direction perpendicular to the substrate (Z direction). That is, with the electrostatic attractive force generated between the comb electrodes, the movable portion 108 (not shown in FIGS. 3A to 3D) supporting the movable comb electrode 105 can be driven. Note that, with the electrostatic attractive force, the movable comb electrode 105 is liable to approach the fixed comb electrode 106, but the movable comb electrode 105 receives the electrostatic attractive force substantially equally on the left and right sides in the horizontal direction (X direction), and hence displacement occurs upwardly in the perpendicular direction. As illustrated in FIG. 3B, in a balanced state, the elastic body 109 (not shown in FIG. 3B) plays a role of stopping the movable comb electrode 105 at a position at which the electrostatic attractive force and the restoring force of the elastic body are balanced when the movable comb electrode 105 is displaced by the electrostatic attractive force. As illustrated in FIG. 3C, after voltage release, the electrostatic attractive force between the comb electrodes is released, and hence the balance between the electrostatic attractive force and the restoring force of the elastic body is cancelled. Thus, the restoring force of the elastic body acts on the movable comb electrode 105. As illustrated in FIG. 3D, after displacement, the movable comb electrode 105 returns to the initial position by the restoring force of the elastic body. Note that, in this embodiment, displacement caused by the electrostatic attractive force is described, but displacement may be caused by electrostatic repulsion. In the case of electrostatic repulsion, voltages of the same sign are applied to the movable comb electrode 105 and the fixed comb electrode 106. The magnitude of the voltage is controlled to control the intensity of the electrostatic repulsion. Further, the positive and negative signs of the voltages to be applied to the movable comb electrode 105 and the fixed comb electrode 106 may be opposite to those illustrated in FIGS. 3A to 3D. In other words, in the present invention, the displacement of the movable portion is controlled in accordance with the voltages to be applied to the movable comb electrode and the fixed comb electrode.

In this case, an electrostatic attractive force Fz in the perpendicular direction, which acts when a potential difference is applied between the movable comb electrode 105 and the fixed comb electrode 106, may be represented by the following formula (1):

$$Fz=[(\epsilon_0 \cdot N \cdot h)/(2g)] \cdot (Vm-Vf)^2 \tag{1},$$

where $\epsilon_0$ represents a dielectric constant of vacuum, N represents the number of gaps between the comb electrodes, h represents an overlapping length between the movable comb electrode and the fixed comb electrode, Vm represents a potential of the movable comb electrode, Vf represents a potential of the fixed comb electrode, and g represents a width of the gap between the comb electrodes.

As described above, in the electrostatic comb actuator according to the present invention, the movable comb electrode and the fixed comb electrode are made up of the thick handle layer, and the elastic body is made up of the thin elastic body layer. Thus, the displacement of the movable portion can be increased. Further, the electrostatic comb actuator according to the present invention includes the structure reinforcing portion formed across the handle layer separation groove separately from the elastic body layer, and hence the strength of the connection portion in the separation groove can be increased.

EXAMPLE 1

With reference to FIG. 1, an electrostatic comb actuator according to Example 1 of the present invention is described. The actuator according to Example 1 includes a reinforcing member made up of the insulating layer 104 and the insulating material 112 filled in the handle layer separation groove 110. The substrate 101 in which the electrostatic comb actuator 100 is formed is an SOI substrate including the handle layer 102, the device layer corresponding to the elastic body layer 103, and the insulating layer (BOX layer) 104 sandwiched therebetween. The handle layer of the substrate 101 is made of, for example, p-type monocrystalline silicon having a crystal plane orientation of (100), and has a thickness of, for example, 200 μm and a resistivity of, for example, 0.01 Ωcm to 0.02 Ωcm. The device layer of the substrate 101 is made of, for example, p-type monocrystalline silicon having a crystal plane orientation of (100), and has a thickness of 1 μm and a resistivity of 0.01 Ωcm to 0.02 Ωcm. The insulating layer of the substrate 101 is a BOX layer made of silicon oxide, and has a thickness of, for example, 2 μm.

The electrostatic comb actuator 100 is formed in the SOI substrate with a highly accurate substrate thickness. In particular, the accuracy of the thickness of the elastic body layer 103 is 1 μm±5%. The type, crystal plane orientation, thickness, resistivity of the silicon and the material and thickness of the insulating layer in this example are merely examples, and the present invention is not limited thereto. The movable comb electrode 105 and the fixed comb electrode 106 are made up of the thick handle layer 102 of the SOI substrate. The handle layer separation groove 110 electrically separates the handle layer 101a of the SOI substrate 101, which is connected to the fixed comb electrode 106, from the handle layer 101b of the SOI substrate 101, which is connected to the elastic body 109 supporting the movable comb electrode 105. The handle layer 101a and the handle layer 101b are connected to each other with the insulating layer 104 formed immediately below the handle layer 101a and the handle layer 101b, and the connection portion 111 (located immediately below the separation groove 110) made up of the same elastic body layer 103 as the elastic body 109 provided across the insulating layer 104.

In a case where the insulating layer 104 below the handle layer separation groove 110 is removed, when the elastic body layer 103 is thinned in order to increase the displacement of the movable portion 108 in the direction perpendicular to the substrate, the strength of the connection portion 111 decreases depending on the thickness of the elastic body layer 103. Therefore, in the structure reinforcing portion, the insulating layer 104 is left across the handle layer separation groove 110 in order to increase the strength of the connection portion 111 even when the elastic body layer 103 is thin. In order to further increase the strength, the handle layer separation groove 110 is filled with an insulating material in FIG. 1, which may be omitted when the thickness of the insulating layer 104 is sufficiently large. With this structure reinforcing portion 112, the thickness of the part in which the handle layer separation groove 110 is provided increases, and hence even when the elastic body layer 103 is thin, the strength of the connection portion 111 can be increased while achieving electrode separation. As the insulating material 112 filled in the handle layer separation groove 110, low-stress silicon oxide whose raw material is tetraethoxysilane and ozone and formed by CVD is selected. Note that, the insulating material is not limited thereto, and PSG, BSG, BPSG, SOG, a silicon thermally-oxidized film, or the like may be used. Further, in this example, the insulating layer 104 is left unremoved, but the handle layer separation groove 110 may be filled with an insulating material after the insulating layer 104 is removed, to thereby form the structure reinforcing portion across the handle layer separation groove 110.

As described above, in the electrostatic comb actuator according to this example, the movable comb electrode and the fixed comb electrode are made up of the thick handle layer of the SOI substrate, and the elastic body is made up of the thin device layer of the SOI substrate. Thus, the displacement of the movable portion can be increased. Further, the electrostatic comb actuator according to this example includes the structure reinforcing portion formed across the handle layer separation groove separately from the elastic body layer 103, and hence the strength of the connection portion in the separation groove can be increased.

EXAMPLE 2

Figure 4:
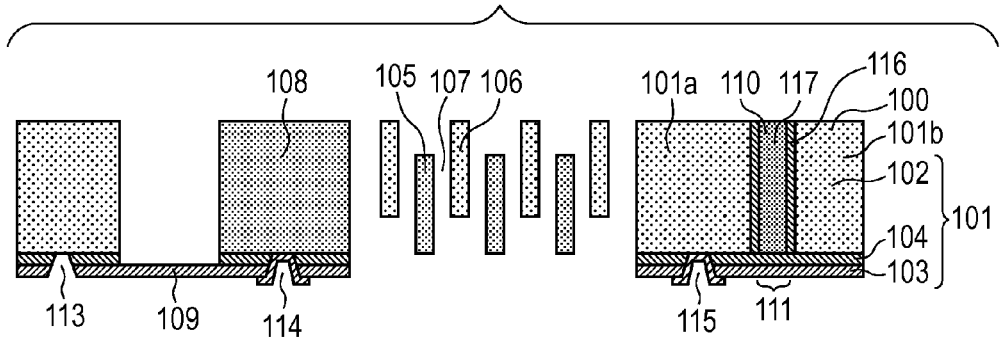
FIG. 4 is a sectional view illustrating an electrostatic comb actuator according to Example 2 of the present invention.

FIG. 4 is a sectional view illustrating an electrostatic comb actuator according to Example 2 of the present invention. The actuator according to this example is different from the configuration of Example 1 in that the handle layer separation groove 110 has an insulating film 116 formed on a side wall thereof, and an insulating material filled in the handle layer separation groove 110 as the structure reinforcing portion is a resin material 117. The substrate 101 is made up of an SOI substrate having the same configuration as that of Example 1.

On the side wall of the handle layer separation groove 110, as the insulating film 116, for example, a silicon thermally-oxidized film is formed so as to have a thickness of, for example, 1 μm. With the insulating film 116, the electrical separation is more reliably achieved between the handle layer 101a connected to the fixed comb electrode 106 and the handle layer 101b connected to the elastic body 109 supporting the movable comb electrode 105. In the structure reinforcing portion, in order to increase the strength of the connection portion 111 even when the elastic body layer 103 is thin, the insulating layer 104 is provided across the handle layer separation groove 110, and the handle layer separation groove 110 is filled with the insulating resin 117. In the structure reinforcing portion, the thickness of the connecting part formed across the handle layer separation groove 110 increases. Therefore, even when the device layer is thin, it is possible to increase the strength of the connection portion 111 while achieving electrode separation.

As the insulating resin material filled in the handle layer separation groove 110, for example, an epoxy-based resin that is thermally cured after being filled in the groove and has small heat contraction is selected. The insulating resin material is not limited thereto, and a resin such as BCB may be used. Further, a resin that is cured by heating is used, but a resin of a type that is cured by ultraviolet light may be selected. Filling of the insulating resin into the handle layer separation groove 110 may be performed under a depressurized condition to perform defoaming inside the groove.

In this example, an insulating resin is used as the material filled in the handle layer separation groove 110, and hence as compared to the case of silicon oxide formed by CVD or the like, the process temperature can be set low. The filling of the insulating resin into the handle layer separation groove 110 can be partially performed merely in the handle layer separation groove 110 after the movable comb electrode, the fixed comb electrode, and the elastic body are formed.

As described above, in the electrostatic comb actuator according to this example, similarly to Example 1, the movable comb electrode and the fixed comb electrode are made up of the thick handle layer, and the elastic body is made up of the thin device layer. Thus, the displacement of the movable portion can be increased. Further, the electrostatic comb actuator according to this example includes the structure reinforcing portion formed across the handle layer separation groove, in which the separation groove is filled with the insulating resin. Thus, the strength of the connection portion in the separation groove can be increased.

EXAMPLE 3

Figure 5:
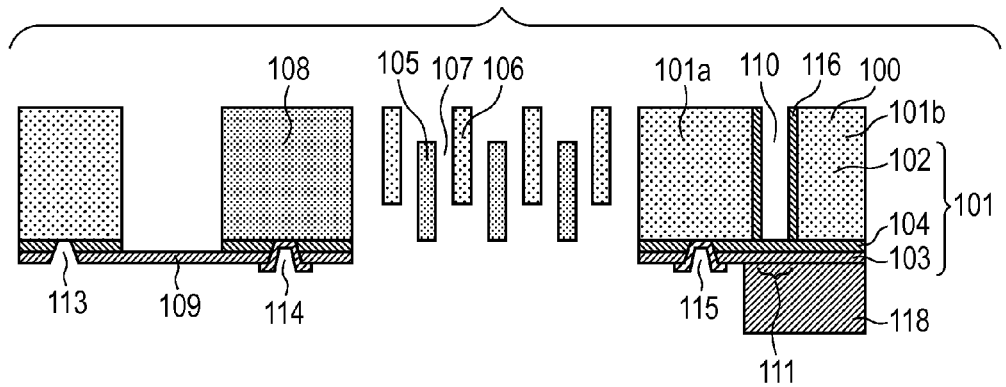
FIG. 5 is a sectional view illustrating an electrostatic comb actuator according to Example 3 of the present invention.

FIG. 5 is a sectional view illustrating an electrostatic comb actuator according to Example 3 of the present invention. The actuator according to this example is different from the configuration of Example 2 in that the actuator according to this example includes, as the structure reinforcing portion, a member formed across the handle layer separation groove 110 and in contact with the elastic body layer 103 on the opposite side to the handle layer 101a, and does not include a material filled in the handle layer separation groove 110. The substrate 101 is made up of an SOI substrate having the same configuration as that of Example 1.

The structure reinforcing portion includes, in order to increase the strength of the connection portion 111 even when the elastic body layer 103 is thin, a base member 118 including an insulating material layer formed across the handle layer separation groove 110 and in contact with the device layer 103 on the opposite side to the handle layer separation groove 110. The base member 118 is a glass substrate and has a thickness of 100 μm. Further, the base member 118 is formed as follows. A glass substrate having a pattern that is formed so as to extend across the handle layer separation groove 110 is adhered by substrate bonding to a region of the substrate 101 corresponding to the connection portion 111. With the base member 118, the thickness of the connection part formed across the handle layer separation groove 110 increases. Therefore, even when the elastic body layer is thin, it is possible to increase the strength of the connection portion 111 while achieving electrode separation.

The base member 118 is a glass substrate provided at a position corresponding to the above-mentioned pattern on the opposite side to the separation groove in a region including a part corresponding to the separation groove so as not to contact with the movable comb electrode 105, the fixed comb electrode 106, the movable portion 108, and the elastic body 109. The substrate material is not limited thereto, and the substrate may be made of an insulating resin or ceramics.

As described above, in the electrostatic comb actuator according to this example, similarly to Example 1, the movable comb electrode and the fixed comb electrode are made up of the thick handle layer, and the elastic body is made up of the thin device layer. Thus, the displacement of the movable portion can be increased. Further, the electrostatic comb actuator according to this example includes, in the region including the part corresponding to the separation groove, the structure reinforcing portion including the insulating material layer formed across the handle layer separation groove and in contact with the elastic body layer on the opposite side to the separation groove. Thus, the strength of the connection portion in the separation groove can be increased.

EXAMPLE 4

Figure 6:
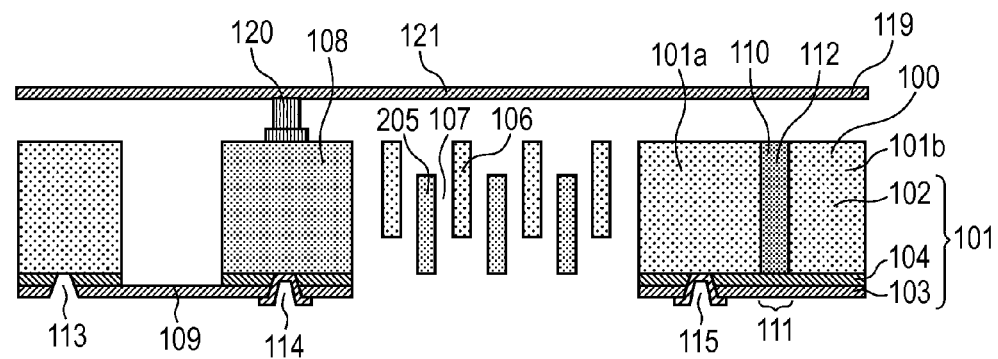
FIG. 6 is a sectional view illustrating a deformable mirror according to Example 4 of the present invention.

FIG. 6 is a schematic sectional view illustrating a deformable mirror according to Example 4 of the present invention. Description of parts of the electrostatic comb actuator 100 similar to those in Example 1 is omitted. Note that, the substrate 101 is made up of an SOT substrate having the same configuration as that of Example 1.

A deformable mirror 119 has a structure in which a mirror (mirror portion) 121 is connected to the movable portion 108 of the electrostatic comb actuator 100 through intermediation of a connection portion 120 formed on the movable portion 108. The deformable mirror 119 can drive the mirror 121 by driving the movable portion 108 of the electrostatic comb actuator 100.

As described above, in the deformable mirror according to this example, the electrostatic comb actuator includes, similarly to Example 1, the movable comb electrode and the fixed comb electrode made up of the thick handle layer, and the elastic body made up of the thin device layer. Therefore, the displacement of the movable portion can be increased. Further, the deformable mirror according to this example includes, similarly to Example 1, the structure reinforcing portion formed across the handle layer separation groove and obtained by filling the handle layer separation groove with an insulating material such as silicon oxide. Thus, the strength of the connection portion in the separation groove can be increased. Further, the structure reinforcing portion is provided to the actuator on the opposite side to the side in which the deformable mirror is provided, or provided so as not to protrude from the surface of the handle layer 101a, and hence large displacement of the deformable mirror is not inhibited.

Note that, in this example, a structure in which a single mirror portion is connected to the electrostatic comb actuator is described, but also a structure in which a single mirror is connected to each of multiple electrostatic comb actuators via the connection portion is possible. With this, the deformable mirror according to this example can individually change the optical length of light reflected by each electrostatic comb actuator portion, and hence the deformable mirror can be used as a wavefront correction device.

EXAMPLE 5

An adaptive optics system that uses the deformable mirror described in Example 4 as a wavefront correction device that compensates for an optical aberration is described with a scanning laser ophthalmoscope (hereinafter described as "SLO apparatus") as an example. The SLO apparatus is an apparatus that irradiates a fundus with light so as to enable observation of a photoreceptor, a retinal nerve fiber layer, hemodynamics, or the like.

Figure 7:
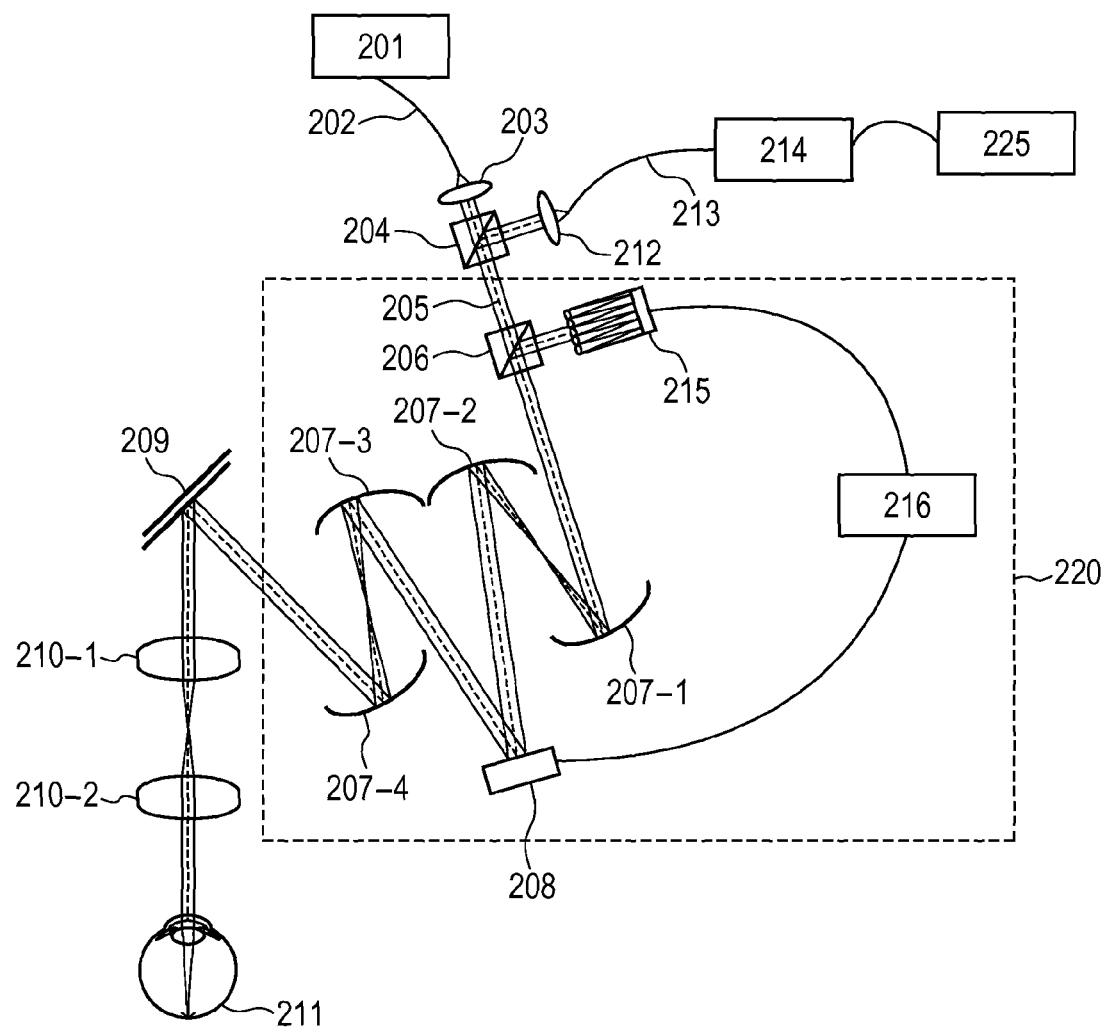
FIG. 7 is a schematic view illustrating an SLO apparatus according to Example 5 of the present invention.

FIG. 7 illustrates a schematic configuration of the SLO apparatus of this example.

Light emitted from a light source 201 travels through a single-mode optical fiber 202 and passes through a collimator 203 to become a collimated light beam. The collimated light beam is transmitted through a beam splitter 204, which serves as light splitting means, as measurement light 205 to be guided to an adaptive optics system 220. The wavelength of the light source 201 is not particularly limited, but particularly for fundus imaging, the wavelength of about 800 nm to 1,500 nm is suitably used for preventing dazzling of a subject and for maintaining the resolution.

The adaptive optics system 220 includes a beam splitter 206 serving as light splitting means, a wavefront sensor (aberration measuring means) 215, a deformable mirror (wavefront correction device) 208, and reflective mirrors 207-1 to 207-4 for guiding the light to those members. The respective reflective mirrors 207 are placed so that at least the pupil of the eye to be inspected, the wavefront sensor 215, and the deformable mirror 208 have an optically conjugate relationship.

The light that has passed through the adaptive optics system 220 is scanned by a light scanning portion 209 one-dimensionally or two-dimensionally. The measurement light scanned by the light scanning portion 209 is radiated to an eye 211 to be inspected through eyepiece lenses 210-1 and 210-2. By adjusting the positions of the eyepiece lenses 210-1 and 210-2, optimum irradiation can be performed in accordance with the visibility of the eye 211 to be inspected. In this case, a lens is used in the eyepiece part, but a spherical mirror or the like may be used instead.

The measurement light radiated to the eye 211 to be inspected is reflected or scattered by a fundus (retina). The light reflected or scattered at the fundus of the eye 211 to be inspected travels, in an opposite direction, a passage similar to that during entrance, and is partially reflected by the beam splitter 206 to enter the wavefront sensor 215. Thus, the wavefront of the light beam is used for measurement. As the wavefront sensor 215, a known Shack-Hartmann sensor can be used.

The reflected and scattered light that has transmitted through the beam splitter 206 is partially reflected by the beam splitter 204 to be guided to a light intensity sensor 214 through a collimator 212 and an optical fiber 213. Light that has entered the light intensity sensor 214 is converted into an electrical signal to be processed into a fundus image by image processing means 225.

The wavefront sensor 215 is connected to an adaptive optics controller 216 to transmit the wavefront of the received light beam to the adaptive optics controller 216. The adaptive optics controller 216 is connected to the deformable mirror 208, which is deformed into a shape instructed by the adaptive optics controller 216.

The adaptive optics controller 216 calculates, based on the wavefront acquired from the wavefront sensor 215, a mirror shape that enables correction into a wavefront with no aberration. Then, in order to reproduce the shape in the deformable mirror 208, a necessary application voltage difference for each of the comb electrodes is calculated and sent to the deformable mirror 208. In the deformable mirror 208, a potential difference sent from the adaptive optics controller 216 is applied between the movable comb electrode and the fixed comb electrode, to thereby deform the mirror surface into a predetermined shape.

The measurement of the wavefront by the wavefront sensor 215, transmission of the wavefront to the adaptive optics controller 216, and instruction by the adaptive optics controller 216 to the deformable mirror for correction of the aberration as described above are repeatedly processed to be feedback controlled to constantly obtain an optimum wavefront.

When the adaptive optics system according to this example is used, the deformable mirror can be significantly moved so that the aberration is compensated for over a wide range. Further, compensation is possible in fast reaction to the instruction from the adaptive optics controller 216. Therefore, the SLO apparatus using the adaptive optics system according to the present invention can appropriately compensate for the aberration generated in the eye to be inspected, and hence high resolution imaging becomes possible.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-248936, filed Nov. 13, 2012, which is hereby incorporated by reference herein in its entirety.

What is claimed is:

1. An actuator comprising:
a support portion;
a movable portion;
an elastic body supporting the movable portion;
a movable comb electrode supported by the movable portion;
a fixed comb electrode supported by the support portion; and
a first wiring applying potential to the movable comb electrode,
wherein the movable portion comprises a first conductive layer, a second conductive layer, and an insulating layer arranged between the first conductive layer and the second conductive layer,
wherein a first contact hole portion is formed in the insulating layer of the movable portion, and
wherein the first wiring is electrically connected to the movable comb electrode via the first contact hole portion and the first conductive layer of the movable portion.

2. The actuator according to claim 1, wherein the elastic body supports the movable portion in such a manner that the movable portion is displaceable in a direction crossing an in-plane of the support portion.

3. The actuator according to claim 2, wherein the movable portion is displaced by the potential applied to the movable comb electrode.

4. The actuator according to claim 1, wherein the second conductive layer of the movable portion serves as a wiring.

5. The actuator according to claim 4, wherein a resistivity of the second conductive layer of the movable portion is 0.01 Ωcm to 0.02 Ωcm.

6. The actuator according to claim 1, wherein the second conductive layer of the movable portion is a part of the elastic body.

7. The actuator according to claim 1, wherein the second conductive layer of the movable portion is monocrystalline silicon.

8. The actuator according to claim 1, wherein the first wiring is electrically connected to a voltage control circuit.

9. The actuator according to claim 1, further comprising a second wiring applying potential to the fixed comb electrode.

10. The actuator according to claim 9, wherein the support portion comprises a first conductive layer, a second conductive layer, and an insulating layer arranged between the first conductive layer and the second conductive layer,
wherein a second contact hole portion is formed in the insulating layer of the support portion, and
wherein the second wiring is electrically connected to the fixed comb electrode via the second contact hole portion and the first conductive layer of the support portion.

11. The actuator according to claim 9, wherein the second wiring is electrically connected to a voltage control circuit.

12. A deformable mirror comprising:
the actuator according to claim 1; and
a mirror portion connected to a movable portion of the actuator.

13. An adaptive optics system comprising:
the deformable mirror according to claim 12;
a wavefront sensor for measuring a wavefront of incident light; and
an adaptive optics controller for calculating a shape of a reflective surface to obtain a wavefront with no aberration, based on the wavefront measured by the wavefront sensor,
wherein the adaptive optics controller controls the actuator so that a reflective surface of the deformable mirror has a calculated shape of the reflective surface.

14. A scanning laser ophthalmoscope comprising:
a light source;
a light scanning portion for scanning light emitted from the light source;
a light intensity sensor for receiving the light intensity of the reflected light from the fundus of an eye to be inspected; and
the adaptive optics system according to claim 13,
wherein the adaptive optics system is arranged on an optical path from the light source to the eye to be inspected.

15. The actuator according to claim 1, wherein the first wiring is electrically connected to the movable comb electrode via the first contact hole portion, the first conductive layer of the movable portion, the second conductive layer of the movable portion, and the elastic body.

16. An actuator comprising:
a support portion;
a movable portion;
an elastic body supporting the movable portion;
a movable comb electrode supported by the movable portion; and
a fixed comb electrode supported by the support portion,
wherein the movable portion comprises a first conductive layer, a second conductive layer, and an insulating layer arranged between the first conductive layer and the second conductive layer,
wherein a contact hole portion is formed in the insulating layer of the movable portion, and
wherein the elastic body is electrically connected to the movable comb electrode via the contact hole portion, the first conductive layer of the movable portion, and the second conductive layer of the movable portion.

17. The actuator according to claim 16, wherein the actuator is configured such that potential is applied to the movable comb electrode by the elastic body.

18. The actuator according to claim 16, wherein the actuator is configured such that potential is applied to the movable comb electrode by the second conductive layer of the movable portion.

19. An actuator comprising:
a support portion;
a movable portion;
an elastic body supporting the movable portion;
a movable comb electrode supported by the movable portion; and
a fixed comb electrode supported by the support portion,
wherein the movable portion comprises a first conductive layer, a second conductive layer, and an insulating layer arranged between the first conductive layer and the second conductive layer,
wherein a contact hole portion is formed in the insulating layer of the movable portion, and
wherein the first conductive layer of the movable portion and the second conductive layer are electrically connected via the contact hole portion.

20. The actuator according to claim 19, wherein the actuator is configured such that potential is applied to the movable comb electrode by the second conductive layer of the movable portion.

* * * * *